(12) United States Patent
Shver

(10) Patent No.: US 6,614,831 B2
(45) Date of Patent: *Sep. 2, 2003

(54) MOUNTING ARRANGEMENT FOR AUXILIARY BURNER OR LANCE

(75) Inventor: Valery G. Shver, Alpharetta, GA (US)

(73) Assignee: Process Technology International, Inc., Tucker, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/902,139

(22) Filed: Jul. 10, 2001

(65) Prior Publication Data

US 2002/0001332 A1 Jan. 3, 2002

Related U.S. Application Data

(63) Continuation-in-part of application No. 09/502,064, filed on Feb. 10, 2000, now Pat. No. 6,289,035.

(51) Int. Cl.$^7$ ................................................. H05B 7/22
(52) U.S. Cl. .............................. 373/66; 373/72; 373/85
(58) Field of Search ............................... 373/66, 72–85, 373/2, 60; 75/10.4, 10.46, 10.19; 266/47, 189

(56) References Cited

U.S. PATENT DOCUMENTS

| | | | |
|---|---|---|---|
| 4,730,336 A | * 3/1988 | Herneisen et al. | 373/2 |
| 5,166,950 A | * 11/1992 | Jouvaud et al. | 110/214 |
| 5,373,530 A | * 12/1994 | Perrin | 266/189 |
| 5,444,733 A | * 8/1995 | Coassin et al. | 266/47 |
| 5,471,495 A | * 11/1995 | Berger et al. | 373/122 |
| 5,802,097 A | * 9/1998 | Gensini et al. | 266/47 |
| 6,212,218 B1 | * 4/2001 | Shver | 373/72 |
| 6,289,035 B1 | * 9/2001 | Shver | 373/2 |
| 6,342,086 B1 | * 1/2002 | Shver | 75/10.4 |
| 6,372,010 B1 | * 4/2002 | Shver et al. | 75/10.4 |

* cited by examiner

*Primary Examiner*—Tu Ba Hoang
(74) *Attorney, Agent, or Firm*—William A. Marvin

(57) ABSTRACT

A mounting enclosure and an improved mounting arrangement for apparatus used in metal melting, refining and processing, particularly those apparatus adapted for steel making in an electric arc furnace, such as burners, lances and the like with supersonic oxygen lancing capability and injectors or the like for the introduction of particulate matter. The mounting enclosure is fluid cooled to survive the hostile environment of the electric arc furnace and is designed to occupy the step between the side wall and hearth of the furnace without any substantial change to the structure of the furnace. The mounting enclosure comprises a plurality of fluid cooling conduits surrounding an apparatus aperture and an injector aperture which are formed through the enclosure and adapted to mount an apparatus and an injector. The mounting arrangement includes utilizing the mounting enclosure to mount an apparatus with supersonic oxidizing gas lancing capability and an injector for particulate carbon in an electric arc furnace. Because the mounting enclosure is approximately the width of the step, the discharge openings of the apparatus and the injector are moved closer to the surface of the melt and toward the center of the furnace thereby providing increased efficiency. The discharge openings will now be extended to near the edge of the step so that the oxidizing gas flow pattern of the apparatus does not degrade the hearth material or other furnace equipment mounted nearby and the carbon flow pattern of the injector sufficiently agitates the slag to produce foaming.

35 Claims, 9 Drawing Sheets

UTILITIES
($H_2O$, GAS,
$O_2$, FLOW
MATERIALS,
ETC.)

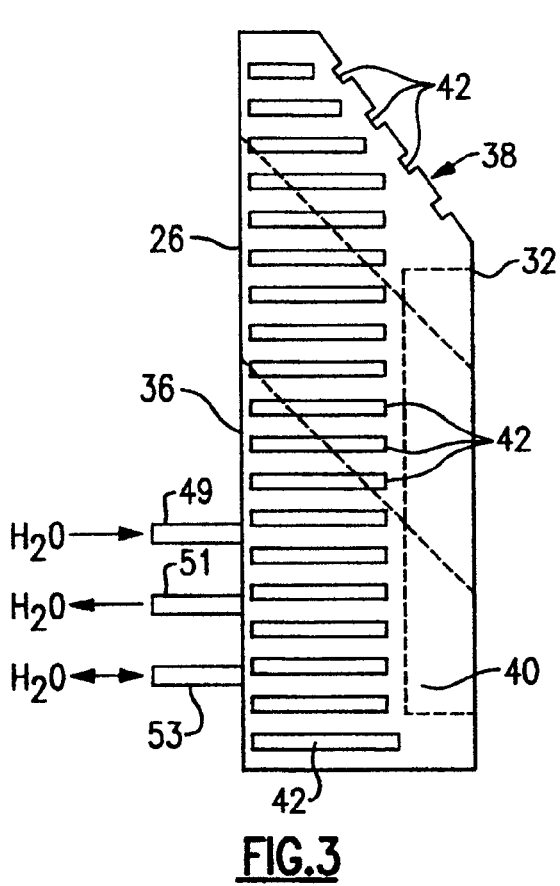
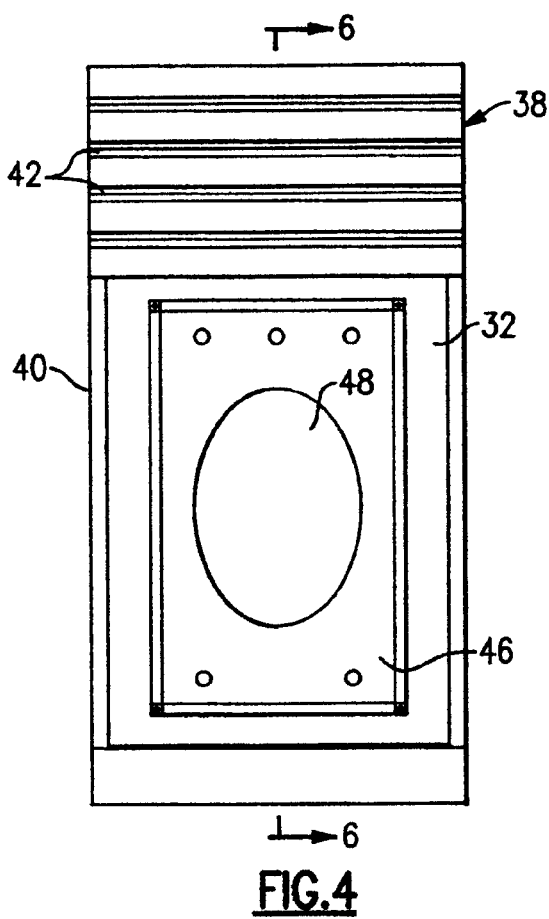
FIG.3
FIG.4
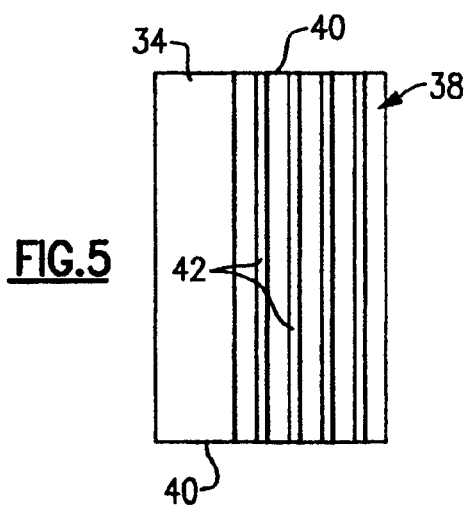
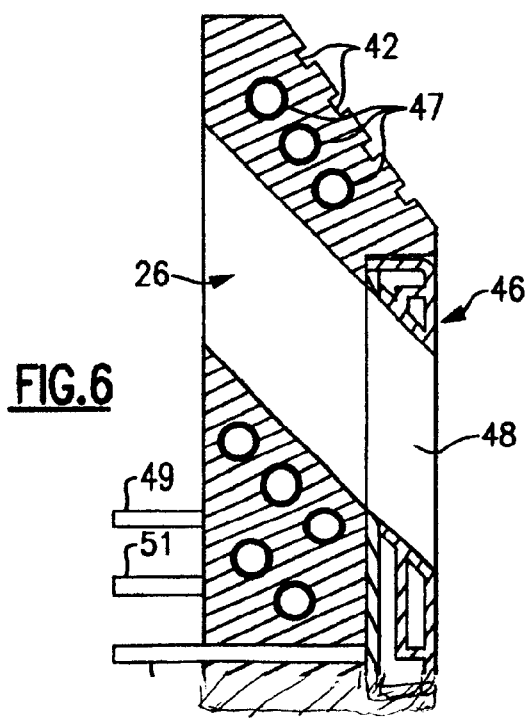
FIG.5
FIG.6

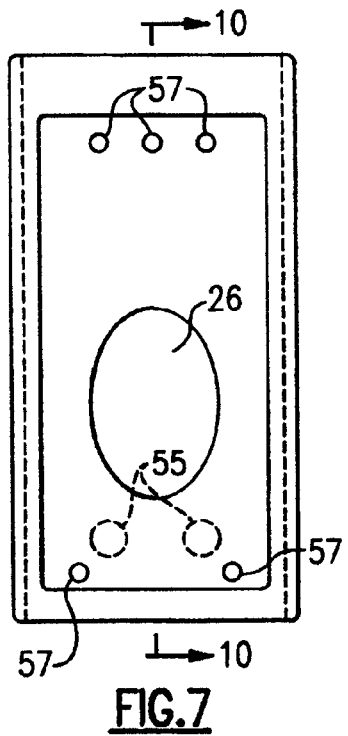
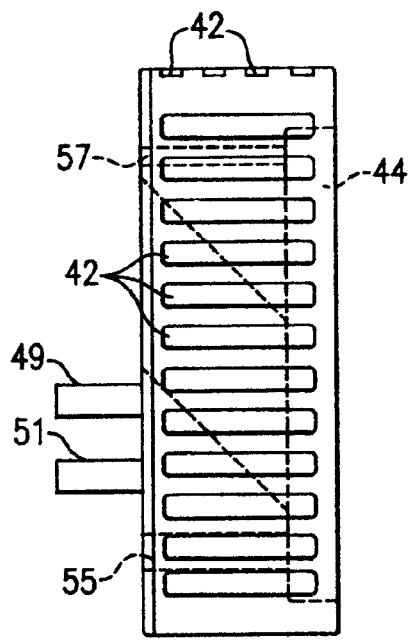
FIG. 7
FIG. 8
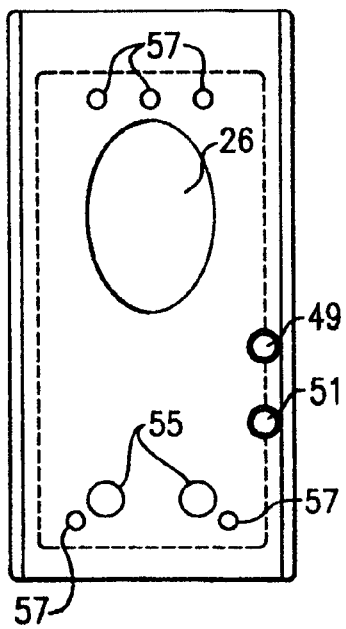
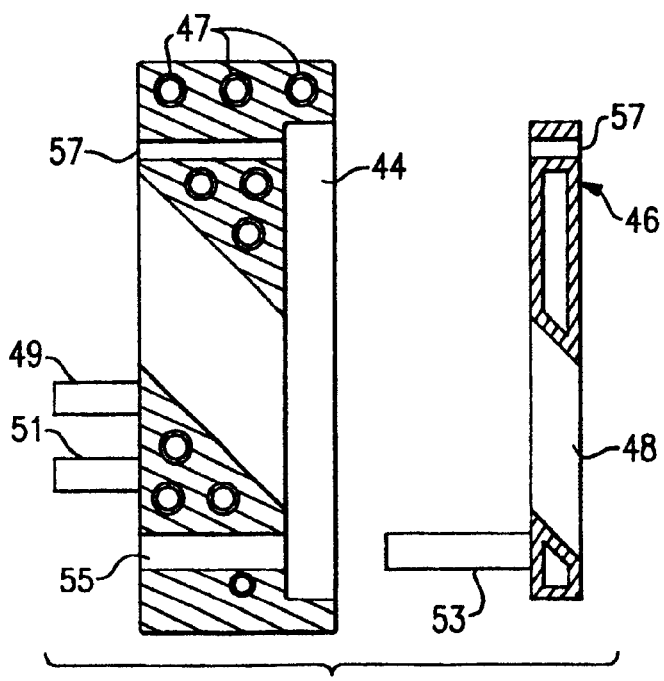
FIG. 9
FIG. 10

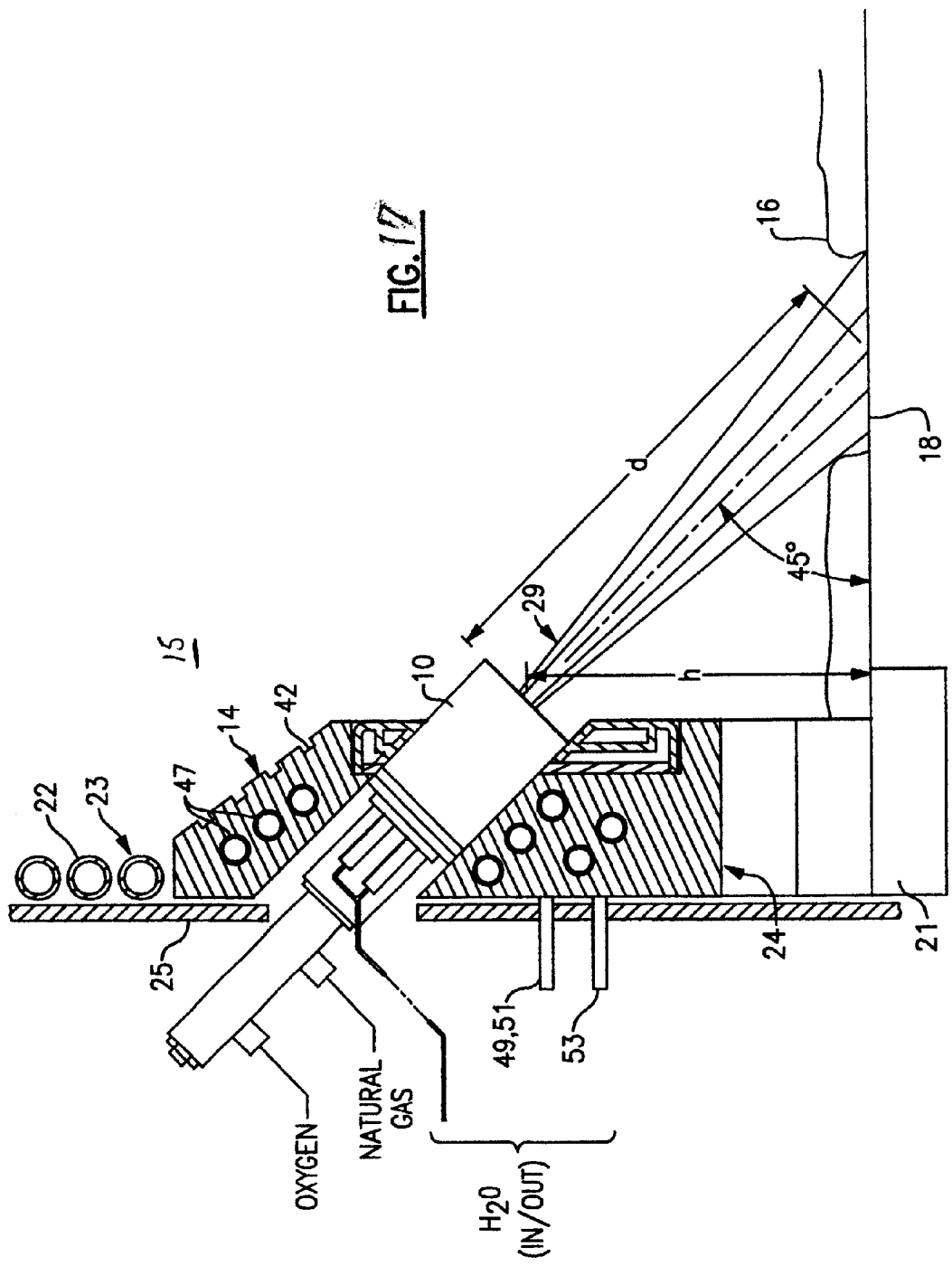

MOUNTING ARRANGEMENT FOR AUXILIARY BURNER OR LANCE

RELATED APPLICATIONS

This application is a continuation in part of application U.S. Ser. No. 09/502,064 filed Feb.10, 2000 by Shver, now U.S. Pat. No. 6,289,035. The disclosure of U.S. Ser. No.: 09/502,064 is hereby incorporated by reference herein.

BACKGROUND OF THE INVENTION

1. Field of the Invention

The present invention generally relates to an improved mounting enclosure and mounting arrangement for apparatus used in metal melting, refining and processing, for example, steel making in an electric arc furnace (EAF), and more particularly, to a mounting arrangement for an auxiliary burner or lance relatively close to a molten metal bath to increase its efficiency.

2. Description of Background Art

An electric arc furnace makes steel by using an electric arc to melt one or more charges of scrap metal which is placed within the furnace. The scrap is charged by dumping it into the furnace through the roof from buckets which also may include charged carbon and slag forming materials. The arc melts the scrap into a molten pool of metal, called an iron carbon melt, which accumulates at the bottom or hearth of the furnace. After a flat bath has been formed by melting of all the scrap introduced, the electric arc furnace enters a refining or decarburizing phase. In this phase, the metal continues to be heated by the arc until the slag forming materials combine with impurities in the iron carbon melt and rise to the surface as slag. When the iron carbon melt reaches a boiling temperature, the charged carbon in the melt combines with any oxygen present in the bath to form carbon monoxide bubbles which rise to the surface of the bath. Generally, at this time supersonic flows of oxygen are blown at the bath with either lances or burners to produce a decarburization of the bath by the oxidation of the carbon contained in the bath. By simultaneously boiling the bath and injecting it with oxygen, the carbon content of the bath is reduced to under 2% carbon whereby the iron carbon melt becomes steel. The carbon in the steel bath is thereafter further reduced until the grade of steel desired is produced, down to less than 0.2% for low carbon steels.

To assist in the steel making process, auxiliary burners or lances can be used for the addition of thermal energy by the combustion of fuel, the injection of oxidizing gas for melt refining, foamy slag production or post combustion of carbon monoxide, and the injection of particulates for slag and foamy slag production. In many instances, the oxidizing gas is introduced as a high velocity stream that may exceed sonic velocities. Laval nozzles, or other supersonic nozzle types, are usually used in the production of high velocity streams of oxidizing gas for injection into a steel making furnace. These supersonic gas flows are produced by the converging/diverging shape of the nozzle which at above a critical pressure causes the gas flow though the nozzle to become supersonic. It is also highly desirable to provide a subsonic flow of oxidizing gas for the burning of fuel, including regular fuel and carbon monoxide for post combustion, for the addition of auxiliary thermal energy, and the supersonic oxygen flow for providing oxygen in iron melt decarburization, assisting in foamy slag production or post combustion of carbon monoxide.

An auxiliary oxy/fuel burner which is useful in the process of steel production in electric arc furnaces and which provides subsonic and supersonic flows of oxygen through the same centrally located conduit is shown to advantage in a technical publication entitled "Advanced Burner Design" by V. Shver, T. Pulliam, and M. Cohen (Shver, et al. I) dated November 1997. This burner is manufactured and commercially sold by Process Technology International, Inc. of Tucker, Ga., the assignee of the present invention. The subsonic flow is produced by providing a pressure in the supply conduit lower than the critical pressure of the supersonic nozzle being used in the conduit. When supersonic oxygen is needed, the pressure in the supply conduit is increased to above the critical pressure. The disclosure of Shver, et al. I is hereby incorporated by reference.

Another burner with the capability to introduce supersonic or subsonic oxidizing gas into an electric arc furnace is illustrated in U.S. Ser. No. 09/251,193, entitled "Method and Apparatus for Improved EAF Steelmaking", filed Feb. 16, 1999 in the name of V. Shver, and assigned commonly with the present application. Shver discloses an annular nozzle for producing a supersonic oxygen flow surrounding a carbon injection conduit forming a portion of a nozzle in a fluid cooled combustion chamber of the burner. The disclosure of Shver is hereby incorporated by reference.

Still another burner with the capability to introduce supersonic or subsonic oxidizing gas into an electric arc furnace is illustrated in U.S. Ser. No. 09/459,303, entitled "Improved Method and Apparatus For Metal Melting, Refining and Processing", filed Dec. 10, 1999 in the names of V. Shver, et al. (Shver, et al. II), and assigned commonly with the present application. Shver, et al. II discloses a supersonic oxygen conduit in a side by side arrangement with a carbon injection conduit forming a portion of a nozzle in a fluid cooled combustion chamber of the burner. The disclosure of Shver, et al. II is hereby incorporated by reference.

Additionally, there are many other burners and lances which provide a supersonic oxidizing gas lancing capability and which provide for the introduction of other materials for use in an electric arc furnace.

The supersonic lancing mode is used in one instance for melt refining because the flow of oxygen must penetrate the molten metal in the hearth of the furnace. The increased velocity of the gas from accelerating it to a supersonic condition increases its momentum and thus depth of penetration into the melt. Another technique to increase the penetrating power of an oxidizing gas flow is to increase the flow rate by the use of a larger supersonic nozzle. While this advantageous to some extent, an excess of oxidizing gas is detrimental to the furnace components and the higher pressures needed for the larger nozzles rapidly become uneconomic.

The mounting of these burners and lances have generally been either through openings in the furnace which are used for other purposes, such as the slag door, roof holes or the EBT access panels, or in greater numbers through specially made openings in the water cooled panels of the side wall of the furnace. The specially made side wall openings allow the burners to be strategically mounted, for example, where there are cold spots in the furnace, or other desired places, possibly for the introduction of process materials. To improve the penetrating power and efficiency of the supersonic oxidizing gas flows from the burners, the mountings of the burners in the furnace side wall have been as far down on the side panels as possible. However, there has been a limit to the mounting of the burners in proximity to the melt because of the structure of many present day furnaces.

The hearth of the furnace is made of refractory materials to contain the molten metal during steel processing. The hearth of the furnace forms a step with the water cooled panels of the furnace side wall where they connect. In the past, the burners have been mounted high enough and at an suitable angle on the side walls where the introduced flows of super sonic oxygen or other materials will miss the edge of the step. Even for those instances where such flows miss the step, the is some deterioration of the refractory by the highly reactive oxidizing gas flowing closely past it. For apparatus providing supersonic oxidizing gas flow this means the mounting angle and flow rates are not only dictated by the steel making process requirements but also by the structure of the furnace.

Therefore, there is a need to mount burners and lances with supersonic oxidizing gas capability closer to the molten metal and directed more to the center of the furnace so they can be more efficient in operation.

There is also a need to mount these burners and lances at optimum angles, to operate them at optimum flow rates and at optimum distances from the melt.

SUMMARY OF THE INVENTION

The invention provides a mounting enclosure for a burner, lance or similar apparatus and an improved arrangement for mounting such apparatus used in metal melting, refining and processing, particularly steel making in an electric arc furnace.

In one preferred embodiment, the mounting enclosure is a fluid cooled free standing block having a mounting aperture for a burner which extends the discharge opening of the burner past the step of the furnace. The preferred implementation of the mounting enclosure includes a front face adapted for the inner part of the furnace, a back face adapted to meet the side wall, and a width approximately that of the step between the side wall and the hearth of the furnace. In this manner, the mounting enclosure can rest on the step and be added to or removed from the furnace without any substantial change to the structure of the furnace. The mounting enclosure is manufactured from a material which is strong enough to withstand the scrap charging and steel and slag splashing of the furnace while also exhibiting a relatively high thermal conductivity. Preferably, the material used for the enclosure is cast iron which is inexpensive and can be easily produced with conduits for fluid cooling and the burner mounting aperture.

In a second preferred embodiment, the mounting enclosure is a fluid cooled box having a mounting aperture for a burner which extends the discharge opening of the burner past the step of the furnace. The preferred implementation of the mounting enclosure includes a front wall with a face adapted for the inner part of the furnace and side walls adapted to meet the furnace side wall of the furnace with a width approximately that of the step between the furnace side wall and the furnace hearth. The mounting enclosure is manufactured from a material which is strong enough to withstand the scrap charging and steel and slag splashing of the furnace while also exhibiting a relatively high thermal conductivity. Preferably, the material used for the mounting enclosure is copper which can be easily produced with conduits for fluid cooling and the burner mounting aperture.

Another aspect of the invention provides the mounting enclosure with a recess in its front face. An fluid cooled insert panel is then installed into the recess to provide additional cooling capacity for the front face of the mounting enclosure. Because the front face of the mounting enclosure may receive the direct radiation from the arc of the furnace, the insert is made out of a material of a high thermal conductivity, which may be the same as the mounting enclosure or even a higher thermal conductivity, preferably copper.

According to another preferred embodiment of the invention, the mounting enclosure further includes a slanted porch between its front face and back face. The slant of the porch lessens the area of the front face directly in line with the radiation of the arc while providing an increased area for fluid cooling. Further, the slant of the porch allows scrap to slide down into the molten bath and away from the mounting enclosure. Optionally, slag retaining means, preferably in the form of cast channels or corrugations, are provided on the porch and the sides of the mounting enclosure to retain a covering of the splashed slag to form a protective barrier over the enclosure.

A first mounting arrangement includes utilizing the mounting enclosure to mount a burner, lance or similar apparatus in a furnace, preferably a burner, lance or similar apparatus with at least supersonic lancing capability and preferably in an electric arc furnace. The burner or lance is mounted by passing it through an aperture in a water cooled side panel aligned with the mounting aperture in the mounting enclosure. Because the mounting enclosure is approximately the width of the step, the discharge opening of the burner is moved by that distance closer to the center of the furnace. The flame discharge opening will now also extend past the inner edge of the sill so that the burner flow pattern is not such a problem to the hearth material and other furnace equipment mounted nearby.

Another mounting arrangement utilizes the walled mounting enclosure to mount a burner, lance or similar apparatus in a furnace. Preferably, the burner, lance or similar apparatus has at least supersonic lancing capability and the furnace is an electric arc furnace. The walled mounting enclosure is inserted through an opening in the side wall of the furnace such that its side walls seal the opening and its front face extends to the edge of the sill. The burner, lance, or similar apparatus is mounted by passing it through the open back of the walled mounting enclosure into the apparatus mounting aperture. Because the mounting enclosure is approximately the width of the step, the discharge opening of the apparatus for burner flame and oxidizing gas lancing is moved by that distance closer to the center of the furnace. The discharge opening of the apparatus will also extend past the edge of the sill so that the burner flow and oxidizing gas flow patterns are not such a problem to the hearth material and other furnace equipment mounted nearby.

Yet another mounting arrangement utilizes the walled mounting enclosure to mount a burner, lance or similar apparatus in combination with a particulate injector in a furnace. Preferably, the burner, lance or similar apparatus has at least supersonic lancing capability, the particulate injector is a carbon injector and the furnace is an electric arc furnace. The walled mounting enclosure is inserted through an opening in the side wall of the furnace such that its side walls seal the opening and its front face extends to the edge of the sill. The burner, lance, or similar apparatus is mounted by passing it through the open back of the walled mounting enclosure into the apparatus mounting aperture. The particulate injector is mounted by passing it through the open back of the walled mounting enclosure into the particulate mounting aperture. Because the mounting enclosure is approximately the width of the step, the discharge opening of the apparatus for burner flame and oxidizing gas lancing is moved by that distance closer to the center of the furnace.

The discharge opening of the apparatus will also extend past the edge of the sill so that the burner flow and oxidizing gas flow patterns are not such a problem to the hearth material and other furnace equipment mounted nearby. Further, the discharge opening of the particulate injector is also moved to the advantageous position.

Advantageously, the apparatus mounting aperture in the mounting enclosure is formed at an optimum angle, preferably 45 degrees for supersonic oxidizing gas flow, for the size and flow rate of the burner being mounted. The distance to the surface of the melt is reduced so that the supersonic oxidizing gas flow rate may be determined by the amount of oxygen needed in the steel making process at a particular point, rather than a larger flow rate needed to produce the required penetration of the melt from farther away. This causes the supersonic oxidizing gas to impinge on the slag and the melt in the furnace at an optimum angle and with an optimum flow rate.

The radiation from the arc increases according to the square of the distance as apparatus is moved closer to the center of the furnace. The mounting enclosure protects the apparatus from this harsh environment while it is located nearer the melt surface and center of the furnace while locating its discharge opening beyond the step to eliminate furnace structure considerations on the burner size and mounting particulars.

According to another aspect of the invention, locating the burner discharge opening nearer the center of the furnace by extending along the step with the mounting enclosure also has the advantage of producing a point of impingement for the oxidizing gas which is closer to the center of the furnace for the same angle and height above the surface. This means more of the oxidizing gas can react with the melt at earlier times in the melting and refining cycle and less reacts with the hearth and other related furnace parts on the outer edge of the process.

These and other objects, aspects and features of the invention will be more clearly understood and better described when the following detailed description is read in conjunction with the attached drawings, wherein similar elements throughout the views have the same reference numerals, and wherein:

BRIEF DESCRIPTION OF THE DRAWINGS

FIG. 3 is a side view of one embodiment of the mounting enclosure illustrated in FIGS. 1 and 2;

FIG. 4 is a front view of the mounting enclosure illustrated in FIG. 3;

FIG. 5 is a top view of the mounting enclosure illustrated in FIG. 3;

FIG. 6 is a cross-sectional side view of the mounting enclosure illustrated in FIG. 3 taken along section line 3A—3A of that figure;

FIG. 7 is a front view of a second embodiment of the mounting enclosure illustrated in FIGS. 1 and 2;

FIG. 8 is a side view of the mounting enclosure illustrated in FIG. 7;

FIG. 9 is a back view of the mounting enclosure illustrated in FIG. 7;

FIG. 10 is a cross-sectional side view of the mounting enclosure illustrated in FIG. 7 taken along section line 7A—7A of that figure;

FIG. 17 is a partially cross-sectioned detailed side view of the improved mounting arrangement for apparatus in an electric arc furnace using the mounting enclosure illustrated in FIGS. 3–6 which has been integrated into the side wall panel of the furnace;

FIG. 18 is a partially cross-sectioned detailed side view of the improved mounting arrangement for apparatus in an electric arc furnace using the mounting enclosure illustrated in FIGS. 7–10 which is used with a side wall panel of the furnace of the spray bar type;

DETAILED DESCRIPTION OF A PREFERRED EMBODIMENT

Figure 1:
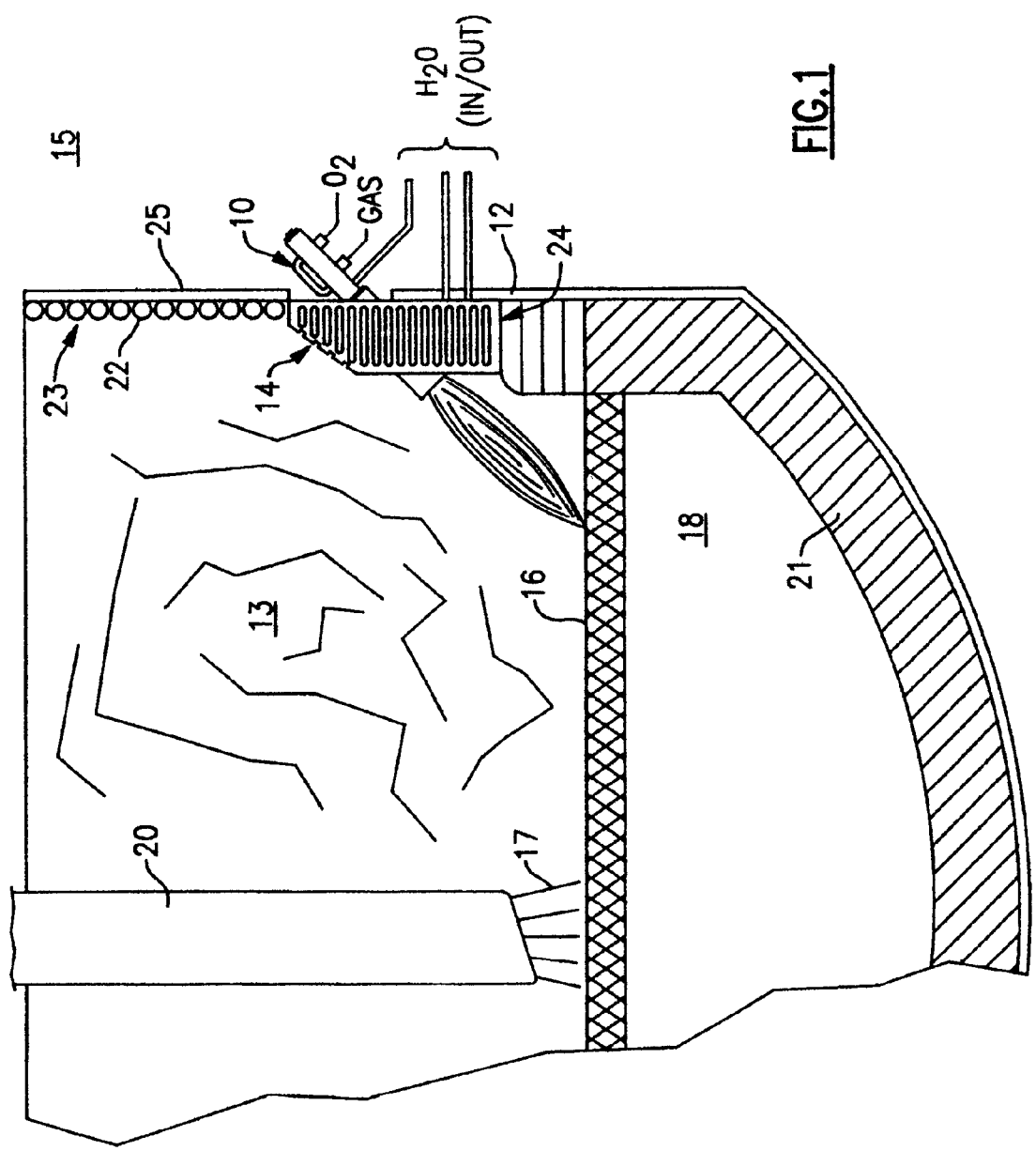
FIG. 1 is a partially cross-sectioned side view of the improved mounting arrangement for apparatus in an electric arc furnace.
Figure 2:
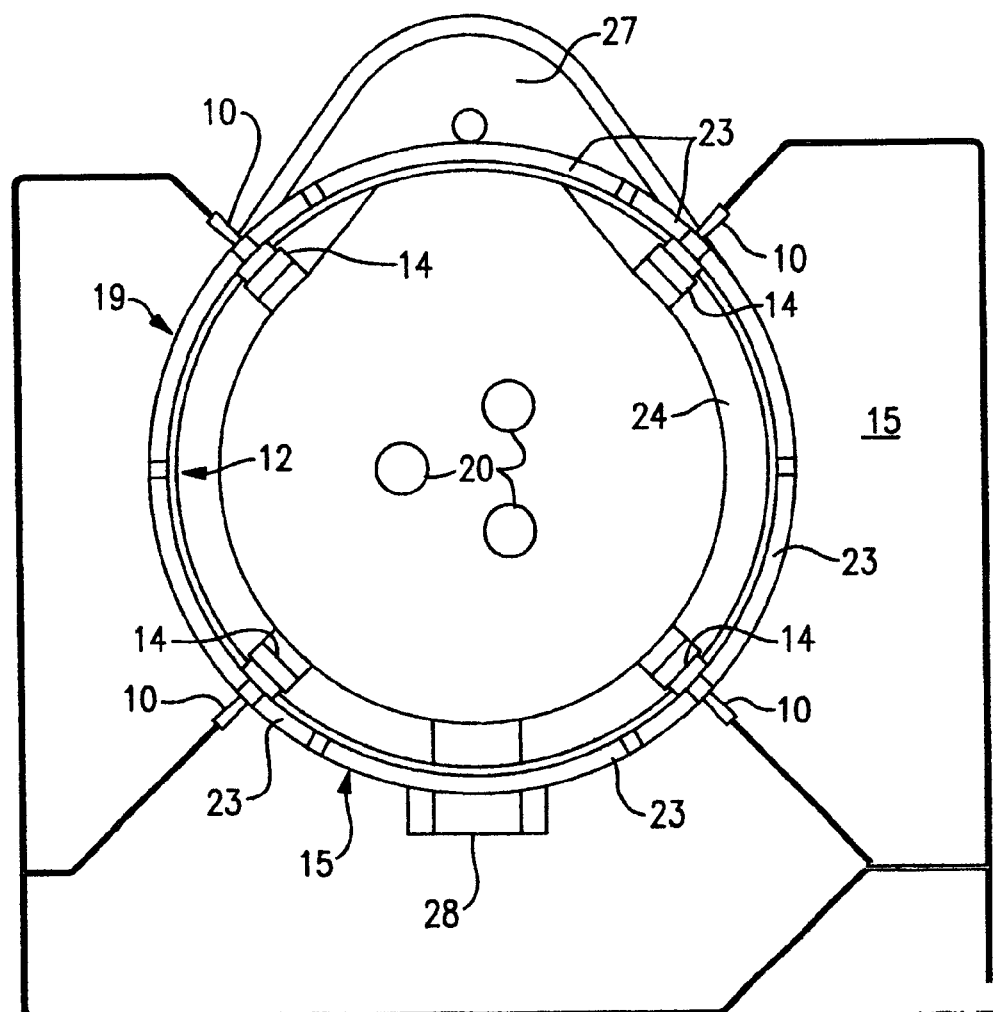
FIG. 2 is a partially cross-sectioned plan view of the mounting arrangement for the electric arc furnace illustrated in FIG. 1.
Figure 11:
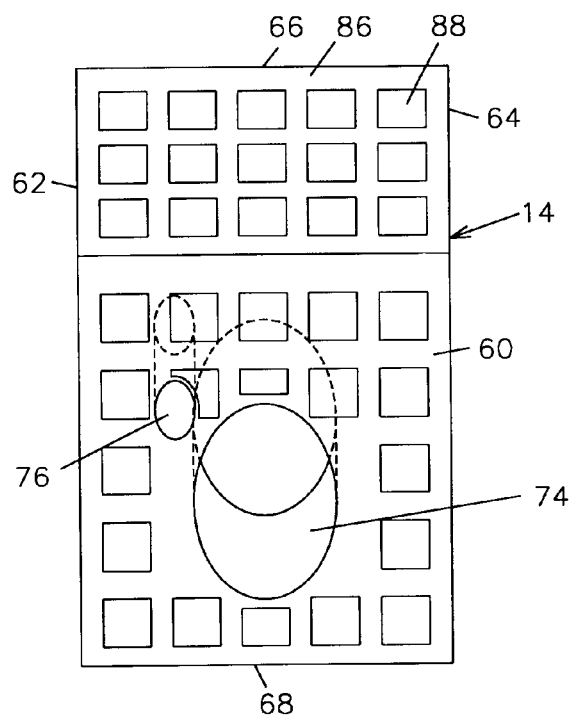
FIG. 11 is a front view of a third embodiment of the mounting enclosure illustrated in FIGS. 1 and 2.
Figure 12:
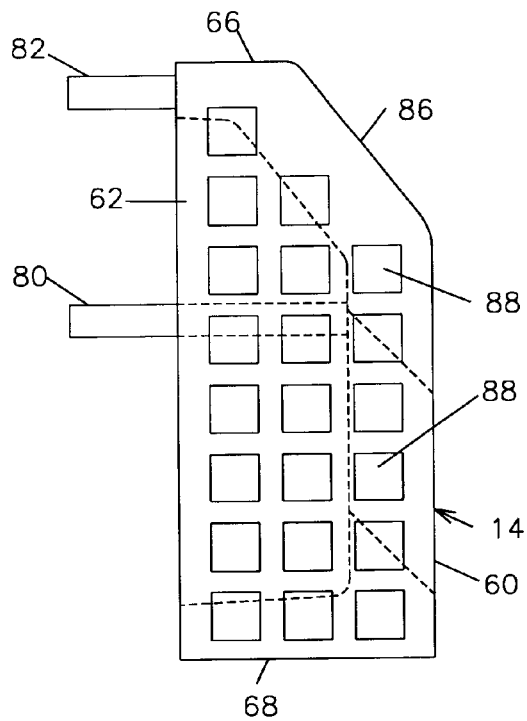
FIG. 12 is a side view of the mounting enclosure illustrated in FIG. 11.

Referring to FIGS. 1 and 2, a plurality of burners 10 are adapted to operate in several different modes to provide auxiliary heating, metal refining and other metallurgical processing capabilities in an electric arc furnace (EAF) 15, or similar metal melting, refining and processing furnaces. Preferably, the burners 10 can be those described previously in the Shver, Shver, et al. I or II references, but they could also be other commercially available air fuel burners, oxygen fuel burners, or oxygen, air fuel burners. Also, while the preferred embodiments of the invention will be described using and mounting such burners, it will be evident that other similar apparatus, such as fixed lances or the like, can be used with the invention to produce advantageous results. The invention will be useful for any metal melting, refining or processing apparatus having a discharge opening whose efficiency can be increased by placing the discharge opening closer to the surface of the molten metal or closer to the center of the furnace. Particularly, the invention will be advantageous for those apparatus, such as the burners and lances, which have a lancing capability with a high velocity oxidizing gas, such as supersonic oxygen.

In FIG. 1 which shows a side view, the EAF 15 melts ferrous scrap 13, or other iron based materials, by means of an electric arc 17 produced from one or more electrodes 20 to collect a molten metal melt 18 at its hearth 21. The generally cup shaped hearth 21 is made of refractory material to withstand the intense heat of the molten metal. The hearth 21 of the EAF 15 is surrounded by an upper shell 19 which is comprised of a series of arcuate fluid cooled panels 23 as best seen in FIG. 2. It is known that the fluid cooled panels 23 forming the side wall 12 of the furnace 15 can be of several conventional types, such as those in the illustrated embodiment with an outer shell member 25 and a plurality of parallel cooling coils 22, an open arrangement of cooling coils with support columns (not shown), or several spray bar arrangements where an inner plate is sprayed with cooling fluid (not shown).

The melt 18 is generally covered with various amounts of slag 16 which is produced by chemical reactions between and the melt and slag forming materials added to the furnace before or during the melting process of the metal. Once the metal has been melted, the metal heat 18 is generally refined or decarburized by oxygen lancing. This reduces the carbon content of the metal to the grade of steel desired. During refining and thereafter, the metal melt 18 is typically heated by the electric arc 17 above its melting temperature. This superheating allows the melt to boil and form further slag from impurities and increases the carbon oxidation with the lanced oxygen. The superheating is also used to allow the metal heat 18 to remain fluid while being transported in a ladle or other carrier to another process step.

The burners 10 are preferably mounted through an opening in the fluid cooling coils 22 of a side wall panel 23 of the furnace 15 into generally rectangular shaped mounting enclosures 14. In the illustrated embodiment, the mounting enclosure 14 preferably rests on the step 24 formed between the panels 23 of the side wall of the upper shell of the furnace 15 and the refractory of the hearth 21, but could also be supported or suspended from a suitable structural member of the furnace. The mounting enclosure 14 is shown located on the inside of the cooling coils 22 of the type of side wall panel 23 having an outer shell member 25. Similarly, such mounting enclosure could be located on the inside of the cooling coils of an open coil type of side wall panel or the inside of a spray bar type side wall panel. When retrofitting an existing furnace with the mounting enclosure 14, this configuration would be preferred because little change to the furnace structure would be needed. For new furnaces, or for newly manufactured replacement shells or panels, the mounting enclosure 14 could also be integrated into the side wall panel 23 by removing the area of cooling coils 22 or the area of spray bars which contact the back face of the enclosure 14.

The burner 10 is received in a mounting aperture 26 of the mounting enclosure 14 so that its discharge opening is extended beyond the edge of the refractory hearth 21. This allows the flow of materials from the discharge opening of the burner 10 to miss the edge of the step so as to not degrade the refractory, particularly with a high velocity oxidizing gas. The mounting of the discharge opening of the burner 10 over the step also brings the material flows from the burner 10 close to the surface of the melt 18 and close to the center of the furnace thereby making the process operation more efficient. The mounting enclosure 14 also provides protection for the burner 10 from the intense heat of the furnace 15 and mechanical damage from falling scrap 13.

The burners, or other apparatus, 10 are typically slanted downward at a mounting angle in the mounting aperture 26, preferably between 30–60 degrees, to direct a material flow 29 from the burner 10 comprised of combustion products, and/or other flows of injected materials, toward the metal melt 18 in the hearth 21 of the furnace. In addition to its downward inclination, the burners, or other apparatus, 10 may also optionally be directed from a radial direction (center of the furnace), preferably from 0–10 degrees. To cause suitable penetration of the melt 18 without splashing a supersonic flow of oxidizing gas, preferably oxygen, should impinge at an angle which is neither too shallow nor too steep. If the angle is too steep, excessive steel and slag splashing may occur. If the angle is too shallow, then the flow may not sufficiently penetrate the surface of the melt 18. Preferably, an angle of around 45 degrees has been found to be efficacious in producing desirable results from high velocity oxidizing gas lancing.

Depending upon the configuration of the furnace 15, as seen in FIG. 2 in plan view, the burners 10 may be mounted anywhere along on the side wall 12 of the upper shell. Individual burners 10 (not shown) may also be mounted in the sump 27 of the furnace 15, if it is an eccentric bottom tapping furnace, or above or in its slag door 28. Generally, a modern furnace 15 has more than one burner, or other apparatus, 10 mounted around its periphery; the number depending upon its size, configuration, melting power and operation.

Generally, such burners 10 are strategically located along the side wall 12 for a number of different purposes, for example, at the cold spots in the furnace to assist with the melting of the scrap. These cold spots are different for DC (Direct Current) furnaces and AC (Alternating Current) furnaces, and may be different even between these furnaces depending on size, manufacturer, and operating procedure of the furnace. Positioning may also depend on other factors such as the materials which are introduced into the furnace by the burner, or other apparatus, 10 and the purpose and timing of its introduction. Other materials which can be introduced include metallurgical and alloying agents, slag forming and foaming agents, oxidizing gases for refining, melting, decarburization, post combustion, etc. The mounting enclosure 14 can be positioned and advantageous mount an apparatus wherever it needs to be on the side wall 12 of the furnace 15.

Whatever other functions or modes the burners, or other apparatus, 10 may have, it is important if an oxidizing gas lancing mode is provided, that they be close to the surface of the melt and directed more to the center of the furnace. The mounting enclosure 14 provides a mounting extension past the water cooled panels 23 of the furnace 15 to allow the discharge opening of a burner 10 to reach beyond the step 24 of the refractory of the hearth 21 and be closer to the center of the furnace.

A first embodiment of the mounting enclosure 14, as seen in one detailed embodiment in FIGS. 3–6, is a generally rectangular cast iron block with a front face 32 for facing the inside of the furnace and back face 36 for abutting the water cooled panel 23 of the furnace upper shell 19. The faces 32, 36 can be flat for ease of manufacture or curved to better conform to conventional circular furnace structure. The thickness of the sides 40 of the mounting enclosure 14 is approximately the width of the refractory of the step 21 so that it can rest on the step with its back face adjacent the side wall panel 23 or furnace upper shell and be self supporting without major structural change to the furnace 15. A mounting aperture 26 is cast at the desired angle of mounting for the burner 10 and is aligned with the opening in the water cooled panel 23. The burner 10 slide mounts into the apertures until its discharge end extends just past the step where it can deliver combustion products, injected materials or, importantly, high velocity oxidizing gas, preferably supersonic oxygen, to the melt 18 without interference from or damage to the refractory of the hearth 21. Surrounding the mounting aperture 26 in the mounting enclosure 14 are cooling channels in the form of coils 47 in which cooling fluid circulates. The coils 47 are connected to inlet pipe 49 and outlet pipe 51 which can be coupled to a supply of cooling fluid under pressure to circulate the fluid through the coils. The cooling fluid, preferably water, cools the surfaces of the mounting enclosure 14 exposed to the furnace heat and the contact surface of the burner with the aperture.

Optionally, the front face 32 and top 34 of the mounting enclosure 14 are connected by a sloping porch 38 which provides several advantageous protective functions. The porch 38 provides a sloping surface along which the scrap 13 may fall into the hearth 21. The porch 38 and sides 40 of the enclosure are also cast with a plurality of generally square channels or corrugations 42. These channels or corrugations 42 are slag retainers which catch a covering of the slag when it splashes on the porch 38 or sides 40 of the enclosure 14. This covering of slag which is less heat conductive than the mounting enclosure 14 further protects the enclosure from the internal heat of the furnace and radiation from the arc 17. It is evident that the channels 42 can be of various other shapes and configurations for retaining the slag.

As better seen in FIGS. 7–10, the mounting enclosure 14 is optionally cast with a recess 44 in the front face 32. An insert panel 46 is installed in the recess 44 of the mounting enclosure 14 and has a mounting aperture 48 aligned with the ones in the mounting enclosure and the side wall 12. The insert panel 46 is preferably fluid cooled and has internal jackets through which a cooling fluid, preferably water, can circulate in the panel. These internal jackets are supplied with the cooling fluid via inlet and outlet connecting pipes 53. The inlet and outlet pipes 53 for the panel insert 46 pass through holes 55 formed in the mounting enclosure 14 for that purpose. One manner of attaching the insert panel 46 to the mounting enclosure 14 is by a plurality of through bolts which pass through holes 57 formed in the mounting enclosure and corresponding holes 59 (only one shown) formed in the insert. The insert panel 46 is preferably manufactured from a material with a high thermal conductivity. Because the panel 46 will face the most intense of the internal heat of the furnace and the radiation from the arc 17, it should be made of a material with the same or even a higher thermal conductivity than the mounting enclosure 14. Preferably, the insert panel 46 is made of copper.

There are at least two, and often three, fluid cooling circuits for a mounting enclosure 14 arrangement. There is a fluid circuit which cools the main enclosure 14, another fluid circuit which cools the insert panel 46 and, optionally, a fluid circuit which cools the burner, or other apparatus, 10. Depending on the cooling needs of the particular installation and the availability of the utility service, the cooling circuits can be independently supplied by individual utility connections or can be serially connected to one supply. A less complex connecting arrangement can be provided with one supply, but the flow rate of the single system must exceed that necessary for the individual component having the highest flow rate. For independent supplies, different flow rates can be used without an undue increase in complexity. For example, the panel insert 46 may necessitate intense cooling and a higher fluid cooling rate than the mounting enclosure 14 which may in turn need a higher cooling rate than the burner 10. It is further evident that any two of the individual components could have a shared supply and the other component an independent supply. An example of this configuration would be where the mounting enclosure 14 and panel insert 46 were one cooling circuit and the burner 10 was coupled to an independent cooling circuit.

Figure 19:
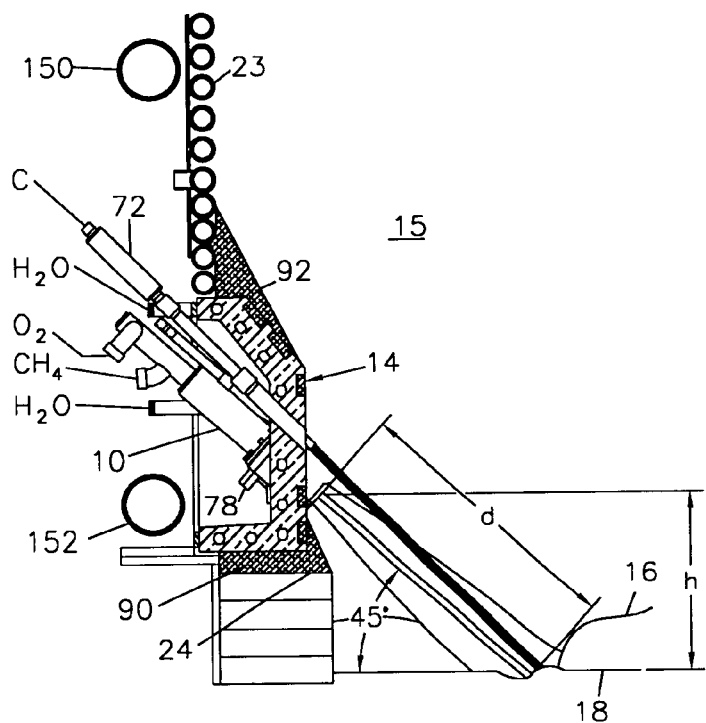
FIG. 19 is a partially cross-sectioned detailed side view of the improved mounting arrangement for apparatus in an electric arc furnace using the mounting enclosure illustrated in FIGS. 11–14 which has been integrated into the side wall panel of the furnace.
Figure 20:
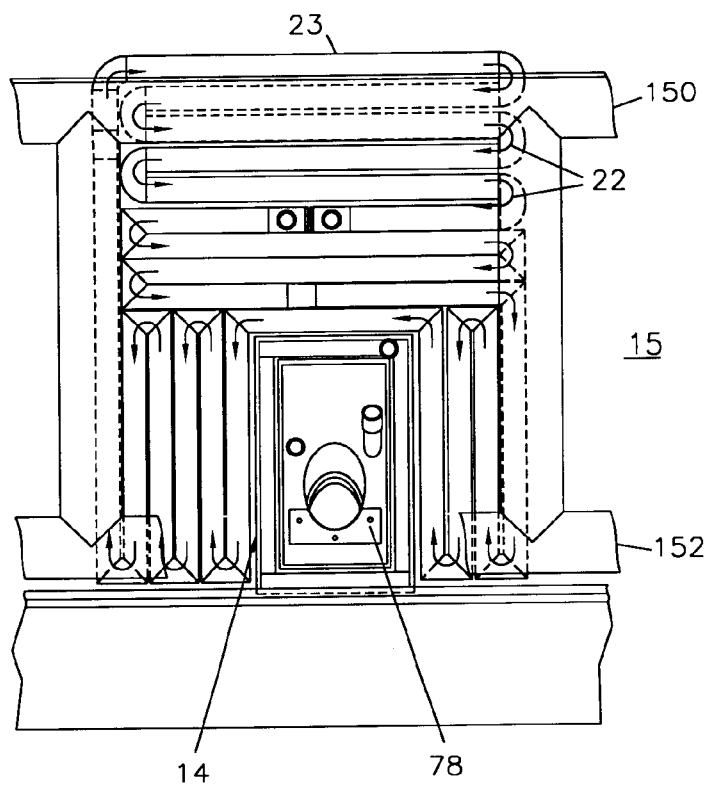
FIG. 20 is a partially broken rear view of the improved mounting arrangement for apparatus in an electric arc furnace using the mounting enclosure illustrated in FIGS. 11–14 which has been integrated into the side wall panel of the furnace.

The mounting enclosure 14, as seen in another detailed embodiment in FIGS. 11–14, can also be a generally open rectangular box. A mounting arrangement utilizing the mounting enclosure of FIGS. 11–14 is illustrated in FIGS. 19 and 20. As better seen in FIGS. 11 and 12, the mounting enclosure 14 has at least a fluid cooled front wall 60 for facing the inside of the furnace and, in the implementation shown, fluid cooled side walls 62, 64, 66 and 68. The mounting enclosure 14 is formed by the front wall 60, top and bottom walls 66 and 68, and lateral side walls 62 and 64 enclosing a space or chamber which is open to the back and which extends the face of front wall 60 out from the water cooled panel 23 of the furnace upper shell 19 near the edge of the step 24 (see FIGS. 2 and 19).

Figure 13:
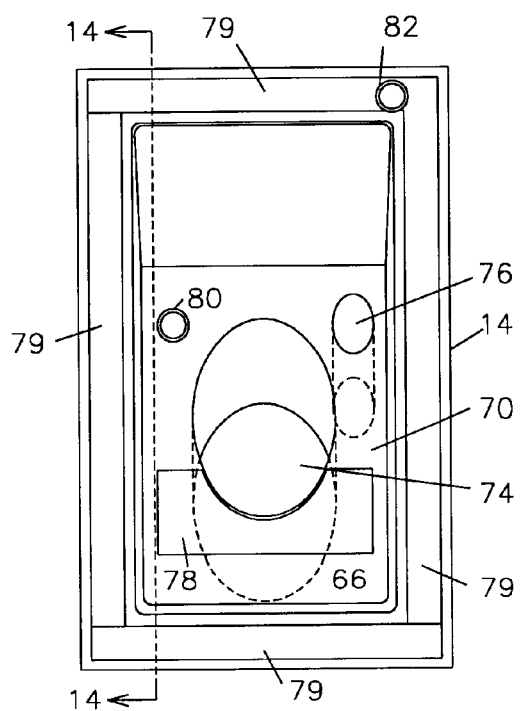
FIG. 13 is a back view of the mounting enclosure illustrated in FIGS. 11.
Figure 14:
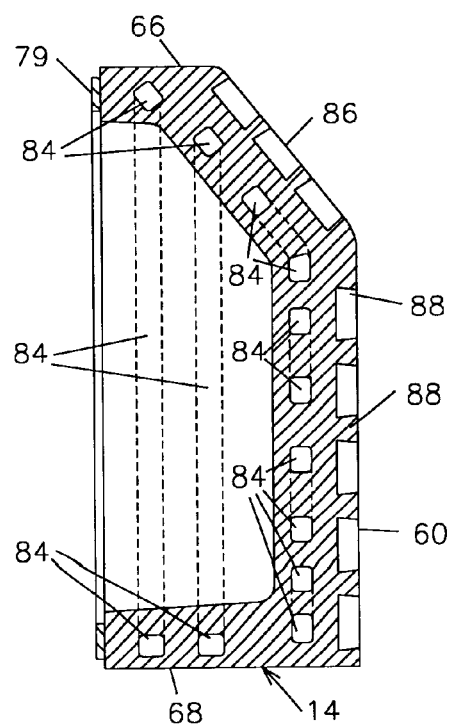
FIG. 14 is a cross-sectional side view of the mounting enclosure illustrated in FIGS. 11 taken along section line 141A-14A of FIG. 13.

With reference now to the rear view of the mounting enclosure 14 in FIG. 13, the front and side walls 60, 62, 64, 66 and 68 define a mounting chamber 70 open to the outside of the furnace for receiving the apparatus 10 and a particulate injector 72 (FIG. 19). The apparatus 10 and particulate injector 72 are inserted through the chamber 70 into an apparatus aperture 74 and an injector aperture 76 formed in the front wall 60. To rigidly fix the apparatus 10 to the mounting enclosure 14, a bracket 78 (FIG. 19) is set at an angle to receive a flange of the apparatus. A series of steel strips 79 may also be welded to the back of the side walls 62, 64, 66, and 68 to provide for a structural attachment of the mounting enclosure 14 to the side wall 23 of the furnace 15.

In FIG. 19, the apparatus 10 slide mounts into the apparatus aperture 74 until its discharge end extends near the edge of step 24 where it can deliver combustion products, injected materials or, importantly, high velocity oxidizing gas, preferably supersonic oxygen, to the slag 16 or melt 18 without interference from or damage to the refractory of the hearth 21. Likewise, the particulate injector 72 slide mounts into the injection aperture 76 until its discharge end extends near the edge of the step 24 where it can deliver injected materials, preferably high velocity particulate carbon, to the slag 16 or melt 18 without interference from or damage to the refractory of the hearth 21.

The apertures 74 and 76 are angled at a injection angle which assists in the penetration of the melt 18 the optimum angle, preferably approximately 45 degrees as illustrated. The central axis of the injection aperture 76 is substantially parallel to the central axis of the apparatus aperture 74. The central axis of the injection aperture 76 in the implementation shown is also to one side of the central axis of the apparatus aperture 74. The side chosen is the downstream side of the reaction zone where slag is exiting because of the circulation of the furnace. Preferably, the configuration allows the particulate injector 72 to inject in the same direction as and substantially parallel to the apparatus 10, preferably a burner/lance, with a particulate pattern which is does not affect the decarburization reaction zone of the burner/lance 10. Optionally, the apparatus aperture 74 and injection aperture 76 may have other configurations such as converging, diverging or even crossing depending upon the various apparatus they mount, the furnace configuration and the process.

The mounting enclosure 14 is preferably formed from a high thermally conductive material such as copper. As shown in cross section in FIG. 14, the mounting enclosure 14 is fluid cooled by circulating a cooling fluid, preferably water, through cooling passages 84 which transit and interconnect all of the sides 60, 62, 64, 66 and 68 of the enclosure 14. The passages 84 are coupled to an input pipe 80 which supplies the cooling fluid under pressure. The cooling fluid flows from the input pipe 80 through the passages 84 in the front wall 60 and into interconnected passages of the lateral side walls 62 and 64. The top and bottom side walls 66 and 68 are also cooled by fluid flowing through interconnected passages 84 before exiting by an output pipe 82.

Optionally, the front wall 60 and top side wall 66 of the mounting enclosure 14 are connected by a sloping porch 86 which provides several advantageous protective functions. The porch 86 provides a sloping surface along which the scrap 13 may fall into the hearth 21. Preferably, the porch 86 and front wall 60 of the enclosure 14 are also made with a plurality of generally rectangular corrugations 88. Optionally, the lateral side walls 62 and 64 may also be formed with the corrugations 88. The corrugations 88 are slag retainers which catch a covering of the slag when it splashes on the porch 86 or walls 60, 62, 64 or 66 of the enclosure 14. This covering of slag which is less heat conductive than the mounting enclosure 14 further protects the enclosure from the internal heat of the furnace 15 and radiation from the arc 17. It is evident that the corrugations 88 can be of various other shapes and configurations for retaining the slag. It is also evident that the corrugations 88 could be filled out with high temperature resistance material, such as ramming refractory, brick, gunning material, etc.

Figure 15:
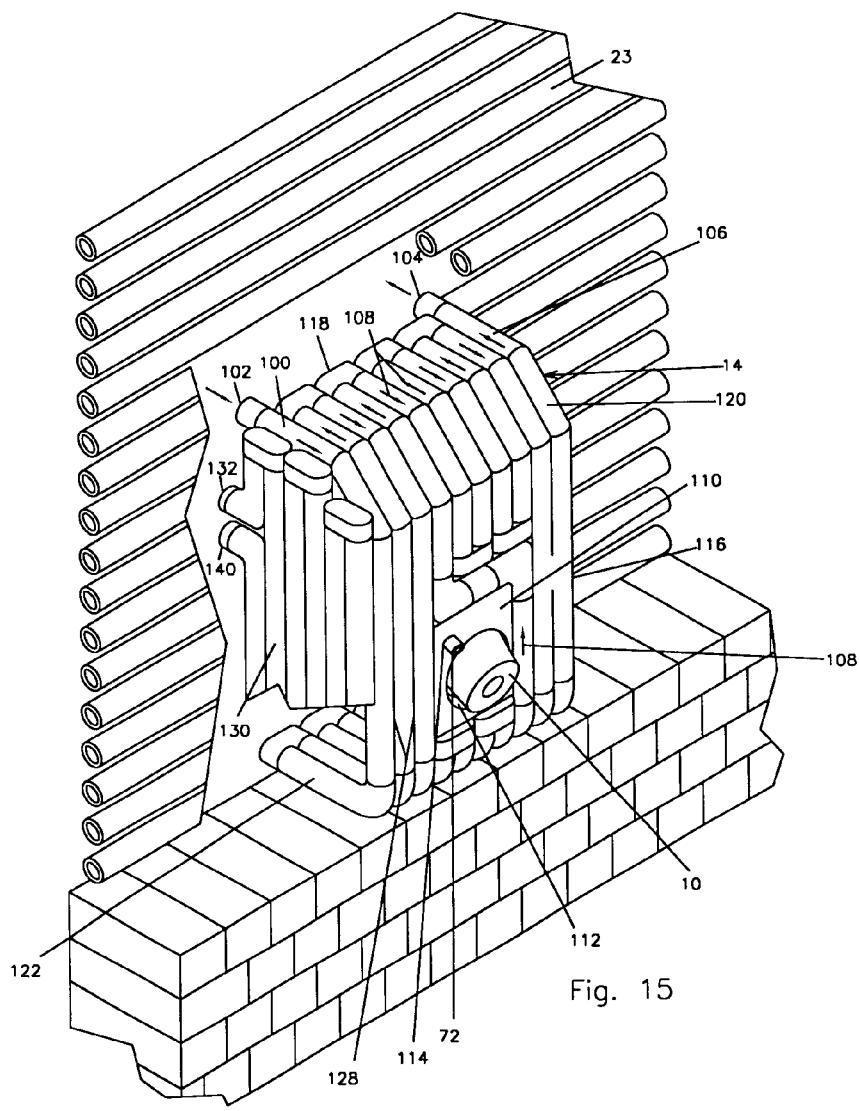
FIG. 15 is a perspective view of a fourth embodiment of the mounting enclosure illustrated in FIGS. 1 and 2.
Figure 16:
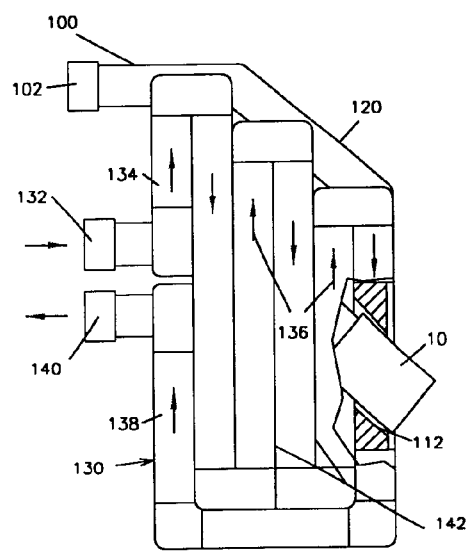
FIG. 16 is a side view of a lateral side wall which can be used in conjunction with the mounting enclosure of FIG. 15.
Figure 13:
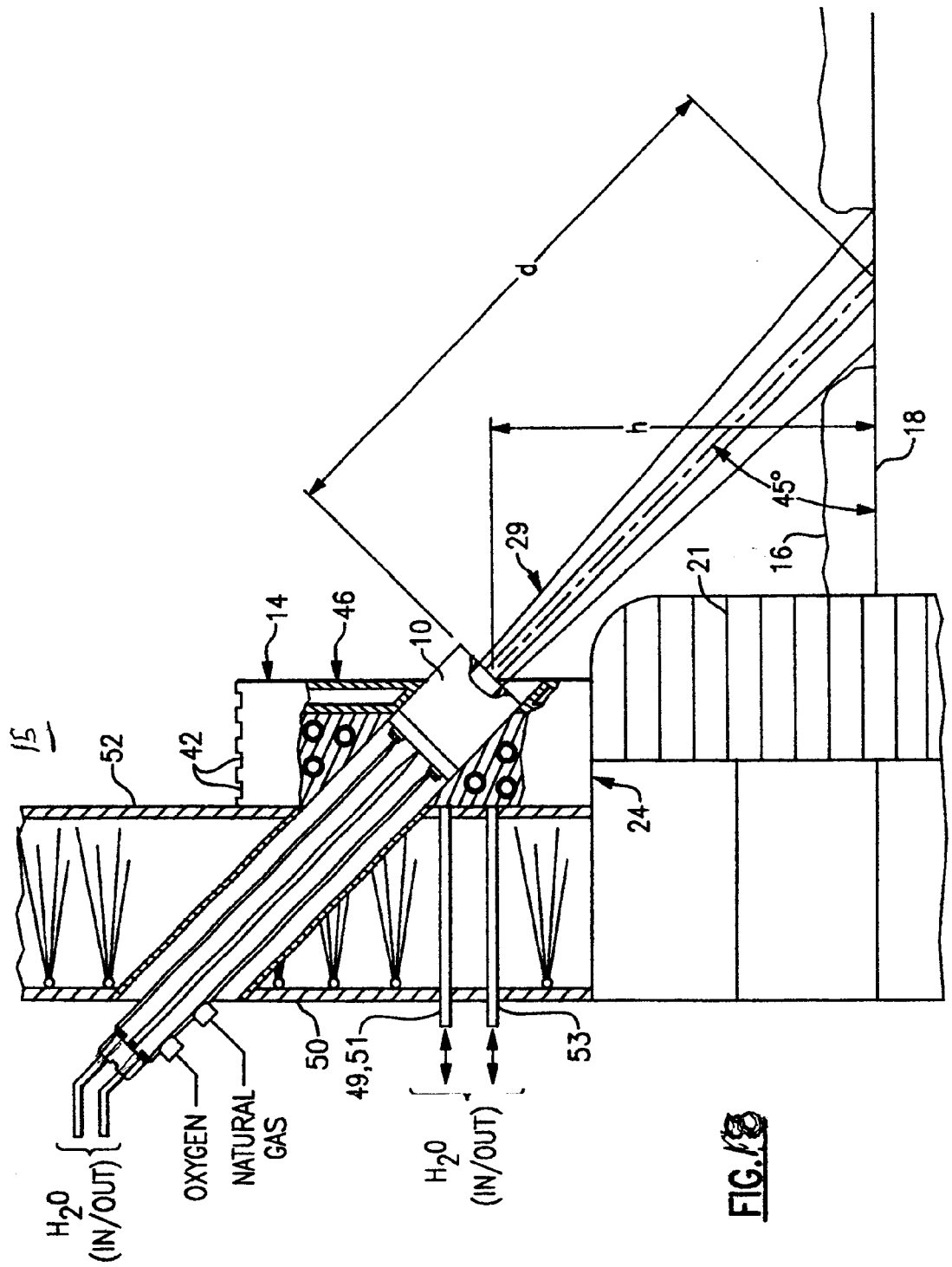

The mounting enclosure 14, as seen in FIG. 15 which details a second implementation of the generally open box embodiment, can comprise a series of connected tubular conduits which are cooled by fluid, preferably water, flowing through them. The enclosure 14 has a cooling fluid under pressure flowing into an end 102 of one conduit 100, circulating through the other conduits and their connections in the directions of the arrows 108, and exiting from an end 104 of another conduit 106. The conduits are preferably manufactured of a high thermally conductive material, such as copper or steel. The conduits are formed to provide a front wall 116 which is able to withstand the intense heat of a surface facing the arc 17 at the edge of the refractory 24, a top wall 118, a porch wall 120 connecting the top wall 118 to the front wall 116, a bottom wall 122, and two lateral side walls 120 (FIG. 16). The porch wall 120 provides scrap deflection for the enclosure and, optionally, could extend upward to where it takes the place of top wall 118. The creases 128 where the conduits come together provide corrugations for retaining slag on the front, top and porch walls to produce a protective covering.

The mounting enclosure 14 is also provided with a insert 110 which is preferably made of a high thermally conductive material, such as copper, steel or the like. The insert 110 is in thermal contact with the conduits of the enclosure 14 and is cooled by them. The insert 110 has an apparatus aperture 112 by which to mount an apparatus 10, preferably a burner/lance, at an injection angle and an injector aperture 114 by which to mount an injector 72, preferably a carbon injector 72, at an injection angle. The central axis of the apparatus aperture 112 and the central axis of the injection aperture 114 are in a similar configuration as that illustrated in FIGS. 11–14, i.e., they are angled at approximately 45 degrees, substantially parallel, and pointed in the same direction. The injection aperture 114 is off to a preferred side of the apparatus aperture 112, for example, the downstream side of the oxygen reaction zone of furnace circulation. The enclosure 14 may be connected to the same cooling circuits as the side wall 23 and affixed to it. In this manner the enclosure 14 can be an integral part of the side wall 23.

Each lateral side wall 130 comprises a series of connected tubular conduits which are cooled by fluid, preferably water, flowing through them. The side wall 130 has a cooling fluid under pressure flowing into an end 132 of one conduit 134, circulating through the other conduits and their connections in the directions of the arrows 136, and exiting from an end 140 of another conduit 138. The conduits of lateral side wall 130 are preferably manufactured of a high thermally conductive material, such as stainless steel or copper. The lateral side wall(s) 130 may be attached to mounting enclosure 14 (FIG. 15) by welding, brackets or other similar methods. The creases 142 where the conduits come together provide slag retaining means. Additional slag retaining means, such as those previously described, can be attached to the pipes of the enclosure 14.

FIG. 17 is a partially cross-sectioned detailed side view of the improved mounting arrangement for apparatus in an electric arc furnace using the mounting enclosure illustrated in FIGS. 3–6 which has been integrated into the side wall panel 23 of the furnace 15. The cooling coils 22 of the panel have been made so as allow the mounting enclosure 14 to directly abut the outer shell member 25. The opening for the burner 10 in the side wall panel 23 is cut in the outer shell member 25 and aligned with the apertures formed in the mounting enclosure 14 and the panel insert 46.

Similarly, FIG. 18 is a partially cross-sectioned detailed side view of the improved mounting arrangement for apparatus in an electric arc furnace using the mounting enclosure illustrated in FIGS. 7–10 which is used with a side wall panel 23 of the furnace of the spray bar type. The burner 10 is mounted through an opening in the spray bar panel 50 and inner shell member 52. The burner 10 may be elongated to span the openings and slide mounts in the apertures in the mounting enclosure 14 and insert panel 46 which are aligned with the openings.

FIG. 19 is a partially cross-sectioned detailed side view of the improved mounting arrangement for an apparatus in an electric arc furnace 15 using the mounting enclosure 14 illustrated in FIGS. 11–14. The mounting enclosure 14 is in thermal contact with the step 24 of the furnace by packing any gap between them with a compressible refractory 90. The top and porch side walls of the enclosure 14 are protected by a slag covering 92 which is retained by the corrugations in the walls. The enclosure 14 can be free standing within the side wall 23 or have an opening cut for the enclosure 14 so that it is open to the outside of the furnace 15. A similar opening could be made in a spray cooled wall panel similar to the one shown in FIG. 18. This allows advantageous access to the equipment protected by the enclosure 14 so that easy mounting for operation and removal for servicing is obtained.

Preferably, the mounting enclosure 14 is integrated into the side wall panel 23 of the furnace 15 as seen in a rear view of the enclosure 14 in FIG. 20. Generally, the side wall panel 23 circulates cooling water from supply to drainage pipes 150, 152 through the cooling coils 22. The cooling coils 22 of the side wall panel 23 have been formed so as allow the mounting enclosure 14 to be inserted through an opening in the panel. The enclosure 14 may be connected to the same cooling circuits as the panel 23 and affixed to it. In this manner the enclosure 14 can be an integral part of the panel 23 and mounted and removed with that panel as one piece.

In FIGS. 17–20 the mounting enclosure 14 mounts the discharge opening of the burner 10 near the edge of the step 24 between the hot face of hearth 21 and the side wall panel 23 and directs the flow from the burner/lance 10 toward the slag 16 and melt 18. As shown, the burner 10 produces a supersonic oxygen stream which penetrates the slag or foamy slag 16 and the melt 18 at approximately a 45 degree angle for providing an optimum utilization of oxygen.

Preferably, the burner/lance 10 has the capability of shrouding the supersonic oxygen flow with an outer flame envelope to produce an even higher penetrating power by the oxygen stream. The mounting arrangement reduces the height (h) of the discharge opening of the burner above the surface of the melt 18 and its overall distance (d) to the melt surface. The mounting of the discharge opening of the burner/lance 10 closer to the surface of the melt and closer to the center of the furnace without destroying the burner/lance increases the oxygne introduction efficiency greatly. The efficiency is also enhanced because an optimum angle of supersonic oxygen flow can be used without damaging the refractory or having to increase oxygen flow rates to produce the necessary velocity for penetration of the melt 18 from longer distances. The mounting enclosure 14 also positions the particulate carbon injector 72 closer to the melt 18 for optimized slag foaming. The close proximity of the injector 72 to the burner/lance 10 helps prevent the injection port of the injector from plugging by slag. It is evident that the mounting arrangements illustrated in FIGS. 17 and 18 could also include an injector aperture for mounting a particulate injector, such as injector 72 that is shown in FIGS. 19 and 20.

Each of the four embodiments, FIGS. 3–6, FIGS. 7–10, FIGS. 11–14 and FIGS. 15–16, have a fluid cooled bottom wall in thermal contact with the refractory of the step 24. The thermal contact by the enclosure 14 advantageously cools the refractory around this area to produces a longer life for the refractory with much less deterioration. This counteracts the increased thermal stress that the refractory near the enclosure may experience because of the exothermic reaction zone for decarburization and heating by the burner flame.

While the invention has been described in connection with several preferred embodiments, the specification is not intended to limit the scope of the invention to the particular forms set forth, but, on the contrary, it is intended to cover any such alternatives, modifications, and equivalents as may be included within the spirit and scope of the invention as defined by the appended claims.

For example, several embodiments have been illustrated as having an injector aperture while several do not. It within the skill of the art to provide each and every implementation with an injector aperture as taught by the detailed description.

For example, each mounting enclosure including those with panel inserts are described as thermally conductive and fluid cooled. It is evident that at least some of the benefits and advantages of those elements described herein could also be provided if either were made of a thermally resistive material such as refractory or the like. It is also evident that either element of a combination of these two elements could be thermally resistive and the other thermally conductive. It is further evident that if one or more of the elements are thermally resistive, they may or may not need supplemental cooling, such as the described fluid cooling.

What is claimed is:

1. A mounting arrangement for an apparatus with a discharge end used in a furnace having a hearth of refractory material which collects molten metal, a plurality of fluid cooled panels forming a side wall, and a refractory step extending a width between the side wall and the hearth, said mounting arrangement comprising:

a mounting enclosure having a width approximately equal to the width of the refractory step, said mounting enclosure having an apparatus aperture adapted to receive the apparatus; and a side wall panel with an aperture adapted to receive said enclosure;

wherein the apparatus when received through said apparatus aperture has its discharge end extended to near the edge of the refractory step.

2. A mounting arrangement for a apparatus as set forth in claim 1 wherein:

said apparatus aperture is aligned at an mounting angle to direct the discharge end of the apparatus toward the molten metal.

3. A mounting arrangement for a apparatus as set forth in claim 2 wherein:

said mounting angle is up to 60 degrees from the horizontal.

4. A mounting arrangement for a apparatus as set forth in claim 1 wherein:

said mounting angle is such that a discharge from the apparatus impinges on the molten metal at between 30–60 degrees from the horizontal.

5. A mounting arrangement for a apparatus as set forth in claim 1 wherein:

said mounting enclosure is fluid cooled.

6. A mounting arrangement for a apparatus as set forth in claim 1 wherein:

said mounting enclosure is manufactured from a material with a high thermal conductivity.

7. A mounting arrangement for an apparatus as set forth in claim 1 wherein:

said mounting enclosure is manufactured at least in part from one of the group consisting of cast iron, steel alloy, copper and combinations thereof.

8. A mounting arrangement for a apparatus as set forth in claim 1 wherein:

said mounting enclosure has a front area adapted to face the inside of the furnace, and a back area adapted to face toward the outside of the furnace.

9. A mounting arrangement for a apparatus as set forth in claim 1 wherein:

said front area of said mounting enclosure includes a recess;

an insert having an insert aperture adapted to receive the apparatus and aligned with the apparatus aperture; and said insert mounting in said recess and made of a material of either high thermal conductivity, thermal resistance, or a combination of high thermal conductivity and high thermal resistance.

10. A mounting arrangement for a apparatus as set forth in claim 9 wherein:

said insert is thermally conductive, fluid cooled, and made of a material with the same as or a higher thermal conductivity than said mounting enclosure.

11. A mounting arrangement for a apparatus as set forth in claim 1 wherein:

said mounting enclosure includes means for deflecting scrap charged in the furnace away from said mounting enclosure.

12. A mounting arrangement for a apparatus as set forth in claim 1 wherein:

said means for deflecting scrap includes a porch sloped toward the inside of the furnace.

13. A mounting arrangement for a apparatus as set forth in claim 12 wherein:

said enclosure includes means for retaining slag to insulate the enclosure from furnace heat.

14. A mounting arrangement for a apparatus as set forth in claim 13 wherein:
   said slag retaining means includes rectangular corrugations located on said porch.

15. A mounting enclosure for an apparatus in a furnace having a hearth of refractory material which collects molten metal and a plurality of fluid cooled panels forming a side wall and having a refractory step extending a width between the side wall and the hearth, said mounting enclosure comprising:
   a fluid cooled enclosure inside of said side wall;
   said enclosure including a front area adapted to face the inside of the furnace, a back area adapted to face the outside of the furnace, and a width between said front area and back area approximately equal to the width of the step;
   an aperture adapted to receive the apparatus; and
   a porch having a corrugated slope toward the inside of the furnace for deflecting charged scrap away from the mounting enclosure and for maintaining a slag covering,
   wherein said apparatus aperture is aligned at an mounting angle of between 20 and 50 degrees from the horizontal to direct the discharge end of the apparatus toward the molten metal and wherein the apparatus when received through said apparatus aperture extends near the edge of the step.

16. A method for mounting an apparatus with a discharge end used in a furnace having a hearth of refractory material which collects molten metal and a plurality of fluid cooled panels forming a side wall with a refractory step extending a width between the side wall and the hearth, said molten metal circulating in the furnace in a preferred direction, said method of mounting comprising:
   mounting the apparatus such that its discharge end extends near the edge of the step in the furnace;
   directing the apparatus at a mounting angle of between 30–60 degrees from the horizontal direction to direct the discharge end of the apparatus toward the surface of the molten metal; and
   directing the apparatus at a mounting angle of between 0–20 degrees from a radial direction to the center of the furnace to direct the discharge end of the apparatus in the direction of the melt circulation of the furnace.

17. A mounting arrangement for a plurality of apparatus with discharge ends used in a furnace having a hearth of refractory material which collects molten metal and a plurality of fluid cooled panels forming a side wall and having a refractory step extending a width between the side wall and the hearth, said mounting arrangement comprising:
   a mounting enclosure having a width approximately equal to the width of the refractory step, said mounting enclosure having a first aperture adapted to receive a first apparatus and a second aperture adapted to receive a second apparatus;
   at least one of the wall panels adapted to receive the enclosure;
   wherein the first apparatus when received through said first aperture has its flame discharge end extending near the edge of said step; and
   wherein the second apparatus when received through said second aperture has its flame discharge end extending near the edge of said step.

18. A mounting arrangement for a apparatus as set forth in claim 17 wherein:
   said first aperture is aligned at a first mounting angle to direct the discharge end of the first apparatus toward the molten metal; and
   said second aperture is aligned at a second mounting angle to direct the discharge end of the second apparatus toward the molten metal.

19. A mounting arrangement for a apparatus as set forth in claim 18 wherein:
   said first mounting angle is between 30–60 degrees from the horizontal; and
   said second mounting angle is between 30–60 degrees from the horizontal.

20. A mounting arrangement for a apparatus as set forth in claim 17 wherein:
   said mounting enclosure is fluid cooled.

21. A mounting arrangement for an apparatus as set forth in claim 17 wherein: said mounting enclosure is manufactured from one material with a high thermal conductivity of the group consisting of cast iron, stainless steel, and copper.

22. A mounting arrangement for a apparatus as set forth in claim 17 wherein:
   said mounting enclosure has a front area adapted to face the inside of the furnace, and a back area adapted to face toward the outside of the furnace.

23. A mounting arrangement for a apparatus as set forth in claim 17 wherein:
   said mounting enclosure includes means for deflecting scrap charged in the furnace away from said mounting enclosure.

24. A mounting arrangement for a apparatus as set forth in claim 23 wherein:
   said means for deflecting scrap includes a porch sloped toward the inside of the furnace.

25. A mounting arrangement for a apparatus as set forth in claim 17 wherein:
   said enclosure includes means for retaining slag to insulate the enclosure from furnace heat.

26. A mounting arrangement for a plurality of apparatus with discharge ends used in a furnace having a hearth of refractory material which collects molten metal and a plurality of fluid cooled panels forming a side wall and having a refractory step extending a width between the side wall and the hearth, said mounting arrangement comprising:
   a fluid cooled side wall panel adapted to receive a mounting enclosure;
   said mounting enclosure being fluid cooled and mounted inside of said side wall, said mounting enclosure having a front area adapted to face the inside of the furnace, a back area adapted to face the outside of the furnace, a width between said front area and back area approximately equal to the width of said step, a porch having a corrugated slope toward the inside of the furnace for deflecting charged scrap away from said mounting enclosure and means for maintaining a slag covering, and said mounting enclosure further having a first aperture adapted to receive a first apparatus and a second aperture adapted to receive a second apparatus;
   wherein said first and second apertures are aligned at a mounting angle of up to 60 degrees from the horizontal to direct the flame discharge ends of the first and second apparatus toward the molten metal; and
   wherein the first and second apparatus when received through said first and second apertures have their flame discharge ends extending near the edge of said step.

27. A mounting enclosure for an apparatus in a furnace having a hearth of refractory material which collects molten metal and a plurality of fluid cooled panels forming a side wall and having a refractory step extending a width between the side wall and the hearth, said mounting enclosure comprising:
   a fluid cooled enclosure for mounting inside of the side wall;

said enclosure including a front area adapted to face the inside of the furnace, a back area adapted to face outside of the furnace, and a width between said front area and back area approximately equal to the width of the step;

a first aperture adapted to receive a first apparatus;

a second aperture adapted to receive a second apparatus;

a corrugated porch sloped toward the inside of the furnace for deflecting charged scrap away from said mounting enclosure;

means for maintaining a slag covering, wherein said first aperture and second aperture are aligned at an mounting angle of between 20 and 50 degrees from the horizontal to direct the discharge ends of the first and second apparatus toward the molten metal and wherein the discharge ends of the first and second apparatus when received through said first and second apertures extend near the edge of the step.

28. A method for mounting a plurality of apparatus with discharge ends used in a furnace having a hearth of refractory material which collects molten metal and a plurality of fluid cooled panels forming a side wall with a refractory step extending a width between the side wall and the hearth, said molten metal circulating in the furnace in a preferred direction, said method of mounting comprising:

mounting a first apparatus such that its discharge end extends near the edge of the step in the furnace;

directing said first apparatus at a mounting angle of between 30–60 degrees from the horizontal direction to direct the discharge end of the apparatus toward the surface of the molten metal;

directing said first apparatus at a mounting angle of between 0–20 degrees from a radial direction to the center of the furnace to direct the discharge end of the apparatus in the direction of the melt circulation the of the furnace; and mounting a second apparatus such that its discharge end extends near the edge of the step in the furnace;

directing said second apparatus at a first mounting angle of between 30–60 degrees from the horizontal direction to direct the discharge end of the apparatus toward the surface of the molten metal; and directing said second apparatus at a second mounting angle of between 0–20 degrees from the radial direction to the center of the furnace to direct the discharge end of the apparatus toward the circulation the of the furnace.

29. A mounting arrangement for an apparatus with a discharge end used in a furnace having a hearth of refractory material which collects molten metal, a plurality of fluid cooled panels forming a side wall, and a refractory step extending a width between the side wall and the hearth, said mounting arrangement comprising:

a mounting enclosure for mounting the apparatus and adapted to be mounted inside of said side wall; and said mounting enclosure having a width approximately equal to the width of the refractory step and having a cooling area in thermal contact with the refractory step.

30. A mounting arrangement for an apparatus as set forth in claim 29 wherein:

said cooling area transfers heat to at least one portion of said mounting enclosure which is fluid cooled.

31. A mounting arrangement for an apparatus as set forth in claim 29 wherein:

said mounting enclosure includes a bottom face in thermal contact with the refractory step.

32. A mounting arrangement for an apparatus as set forth in claim 31 wherein:

at least said bottom face of said mounting enclosure is fluid cooled.

33. A mounting arrangement for an apparatus as set forth in claim 32 wherein:

said mounting enclosure is a fluid cooled block.

34. A mounting arrangement for an apparatus as set forth in claim 32 wherein:

said mounting enclosure is a fluid cooled box having at least a front wall and a bottom wall.

35. A mounting arrangement for an apparatus as set forth in claim 34 wherein:

said mounting enclosure is formed of thermally conductive conduit.

* * * * *